United States Patent [19]
Omara et al.

[11] Patent Number: 6,103,098
[45] Date of Patent: Aug. 15, 2000

[54] METHOD OF SENSING EXHAUST OXYGEN

[75] Inventors: Ahmed Abdelaziz Omara, Ann Arbor; Eleftherios Miltiadis Logothetis, Birmingham; Richard E. Soltis, Saline, all of Mich.

[73] Assignee: Ford Global Technologies, Inc., Dearborn, Mich.

[21] Appl. No.: 09/089,804

[22] Filed: Jun. 3, 1998

[51] Int. Cl.⁷ .................................................. G01N 27/407
[52] U.S. Cl. ...................... 205/784.5; 204/426; 204/429
[58] Field of Search ................................. 204/421–429; 205/783.5, 784, 784.5, 785

[56]  References Cited

U.S. PATENT DOCUMENTS

| | | |
|---|---|---|
| 4,101,403 | 7/1978 | Kita et al. ............................... 204/429 |
| 4,189,355 | 2/1980 | Fujishior et al. . |
| 4,304,652 | 12/1981 | Chiba et al. . |
| 4,487,680 | 12/1984 | Logothetis et al. . |
| 4,500,412 | 2/1985 | Takahashi et al. . |
| 4,505,783 | 3/1985 | Mase et al. . |
| 4,510,036 | 4/1985 | Takeuchi et al. ....................... 204/425 |
| 4,724,061 | 2/1988 | Nyberg . |
| 4,882,033 | 11/1989 | Shibata et al. . |
| 5,164,068 | 11/1992 | Udo et al. . |
| 5,178,744 | 1/1993 | Nakazawa et al. . |
| 5,389,225 | 2/1995 | Aagard et al. . |

*Primary Examiner*—T. Tung
*Attorney, Agent, or Firm*—Jennifer Stec; Roger L. May

[57] ABSTRACT

A method of operating an oxygen sensor in the exhaust stream of an engine. The oxygen sensor includes a zirconia plate (14) mounted to two electrodes (16,18), covered with porous layers (20,22). The two porous layers (20,22) are designed to sense the two conditions of air/fuel mixture, lean and rich, by creating a delay in the sensing of the rate of transmission of oxygen through one of these layers (20,22). The method includes flowing exhaust gas over the sensor, maintaining essentially no flow of current through the leads when the exhaust gas maintains a state of rich or lean air/fuel ratio, and sensing induced emf spikes between the leads as the exhaust gas stream transitions between rich and lean air/fuel ratios.

3 Claims, 2 Drawing Sheets

METHOD OF SENSING EXHAUST OXYGEN

FIELD OF THE INVENTION

The present invention relates to oxygen sensors and particularly to oxygen sensors employed in the exhaust systems of internal combustion engines.

BACKGROUND OF THE INVENTION

Automotive vehicles with an internal combustion engine have an exhaust system that includes a pathway for exhaust gas to move away from the engine. The temperature of the exhaust gases ranges from ambient temperature, when the engine has not been run recently, to higher than 1000° Celsius. Frequently used in these exhaust systems is an Exhaust Gas Oxygen (EGO) sensor assembly, which allows for a determination of a rich or lean air/fuel ratio.

The sensing element of an EGO sensor consists of a dense oxygen-conducting zirconia ($ZrO_2$) ceramic, most commonly in the shape of a thimble, with porous platinum electrodes, one on the outside and the other on the inside surfaces of the thimble. The outside electrode is covered with a porous protective layer, e.g., from spinel. This sensing element is mounted onto a spark-plug type of a structure that seals the inside of the thimble from the outside of the thimble. When the EGO sensor is mounted onto the exhaust manifold of an engine, the outer electrode is exposed to the exhaust stream whereas the inner electrode is exposed to the ambient air as a reference oxygen atmosphere. When the air/fuel ratio is lean, the EGO sensor voltage output has a small value (e.g. 50 mV) because the oxygen partial pressure in the exhaust gas is not too different from the oxygen pressure in the air. When the air/fuel is rich, the EGO voltage output is large (e.g., 700–900 mV) because the thermodynamic equilibrium oxygen partial pressure of the exhaust gas is many orders of magnitude smaller than that of the air reference. Consequently, when the air/fuel ratio is changed through the stoichiometric value, the EGO sensor output changes abruptly between a large and a small value. This sensor output signal is obtained by means of an associated set of electrical output leads. This signal is then used by the engine control system to adjust the air-to-fuel mixture being supplied to the combustion chambers of the engine to the desired value, generally very close to the stoichiometric air/fuel ratio.

Most current EGO sensors also include a heater that is inserted in the air reference. The heater assists the zirconia sensor, a heated exhaust gas oxygen (HEGO) sensor, in making more precise measurements over a wide range of exhaust gas temperatures, especially when the exhaust gas temperature is low. The addition of the heater also helps to decrease the light-off time of the sensor, that is the time that it takes for the sensor to reach the minimum temperature for proper operation.

While engine systems utilizing catalysts and HEGO sensors with stoichiometric air/fuel control generally work very well, the hydrocarbon emissions during the cold start phase of engine operation account for approximately half of the total hydrocarbon emissions for new ultra-low emissions vehicles. Consequently, several methods have been developed for reducing cold start hydrocarbon emissions. Many of these are more effective if feedback control of the air/fuel ratio can be accomplished immediately after start-up of the engine. This requires HEGO sensors with reduced light-off times as compared to today's HEGO sensors.

Reduction of light-off times of thimble-type HEGO sensors has been accomplished through the use of high power heaters. However, these times are still generally longer than fifteen seconds because of the large size of the zirconia thimble and the poor thermal coupling of the heater to the thimble. Even with the more recent planar-types of zirconia HEGO sensor configurations, which have smaller thermal mass and better thermal coupling between the heater and zirconia, the light-off times are generally longer than ten seconds.

One method for further decreasing light-off times while using only small or modest heating power is to substantially decrease the size of the zirconia sensing element. This can be more easily accomplished by eliminating the air reference. An example of a sensor without an air reference is illustrated in U.S. Pat. No. 4,304,652 to Chiba et al. This reference describes a planar type sensor have a zirconia layer with one catalytic electrode covered with a porous gas-diffusing layer and one non-catalytic electrode. A DC current is applied to this device which then produces an output voltage that is indicative of air/fuel ratios in the lean range or in the rich range depending on the direction of the current. Good operation of this sensor, however, depends critically on the stability of the two electrodes, especially of the non-catalytic electrode. Unfortunately, this is difficult to accomplish.

It is thus desirable to have an exhaust gas oxygen sensor without an air reference, which not only produces a signal when the air/fuel ratio is changed through stoichiometry, but also that that signal is reproducible and stable over long periods of time, and has minimal thermal mass to reduce the power consumption of the sensor assembly.

SUMMARY OF THE INVENTION

In its embodiments, the present invention contemplates a method of detecting a change from lean to rich and rich to lean air/fuel ratio in the exhaust gas stream of an internal combustion engine. The method comprises the steps of: providing an oxygen sensor having an oxygen-ion conducting solid electrolyte body with a first electrode assembly mounted thereon and a second electrode assembly mounted thereon spaced from the first assembly, with the second assembly having a predetermined time difference in a gas transmission characteristic; providing a pair of leads, each extending from a different one of the electrode assemblies; flowing the exhaust gas over the sensor as the exhaust gas periodically changes from lean to rich and rich to lean; maintaining essentially no flow of current through the leads when the exhaust gas maintains a state of rich air/fuel ratio and when the exhaust gas maintains a state of lean air/fuel ratio; and sensing induced emf spikes between the leads as the exhaust gas stream transitions between rich and lean air/fuel ratios.

Accordingly, an object of the present invention is to provide an exhaust oxygen sensor, having minimal thermal mass, employing an oxygen-ion conducting solid electrolyte body with electrodes mounted thereto, without the need for a reference atmosphere or oxygen pumping through the sensor.

Thus, an advantage of the present invention is that is has a smaller thermal mass, with a faster light-off time than the conventional EGO and HEGO sensors. The sensor can have light-off times of less than three to five seconds, without an excessively large heater element, thus having only moderate power requirements. The quicker light-off time allows for a faster reading of the air/fuel ratio in the exhaust gas for feedback to the engine control system. This, in turn, results in improved emissions.

An additional advantage of the present invention is that the signal produced when the air/fuel ratio passes through stoichiometry is reproducible and stable over long periods of time.

A further advantage of the present invention is that a constant current DC source is not required to drive the sensor, thus further reducing power consumption and cost for the oxygen sensing system.

Another advantage of the present invention is that the induced current spikes due to switches between lean and rich air/fuel ratios can be easily converted to a signal similar to conventional air/fuel sensor outputs without driving a current through the sensor.

DETAILED DESCRIPTION OF THE PREFERRED EMBODIMENTS

Figure 1:
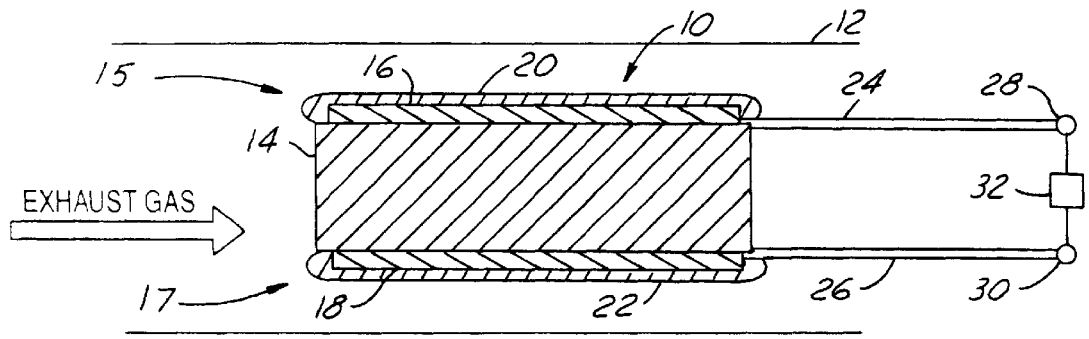
FIG. 1 is a schematic, side view of an oxygen sensor in an exhaust stream in accordance with the present invention.

FIG. 1 shows a sensor assembly 10 in an exhaust pipe 12 having exhaust gas flow over it. The sensor assembly 10 includes a dense ceramic plate 14 of an oxygen-ion conducting solid electrolyte. For example, a plate of fully or partially stabilized zirconia ($ZrO_2$). Contacting either side of the plate 14 are electrode assemblies 15 and 17. The electrode assemblies 15, 17 include gas permeable (i.e., porous) electrodes 16 and 18, respectively, preferably made from platinum. The first electrode 16 is covered with a first porous inert layer 20 and the second electrode 18 is covered with a second porous inert layer 22. These inert layers 20, 22 are preferably made from spinel of alumina. The electrode assemblies 15, 17 are configured so that they have different response times when the exhaust gas composition is changed from lean to rich air/fuel ratio or vice versa. For instance, the layer 20 may be more permeable to gas than the layer 22. Alternately, the second spinel layer 22 can be formed with the same permeability as the first layer 20, but have a greater thickness. Further, rather than create differences between the spinel layers 20, 22, one may configure the electrodes 16, 18 to have different properties; or, some combination of differences between the first electrode assembly 15 and the second electrode assembly 17. Either way, the effect is to change the response time between the two electrode assemblies 15, 17 due to a shift in the exhaust gas composition from lean to rich or vice versa, so that the first assembly 15 has a shorter response time than the second assembly 17.

Extending from the two electrodes 16, 18 are two leads 24 and 26, respectively. The nodes 28 and 30 at the ends of the leads 24, 26 are connected to a signal processor 32 for processing the signal from the sensor assembly 10. This sensor assembly can be fabricated using ceramic tape technology or microfabrication techniques known to those skilled in the art.

Figure 2A:
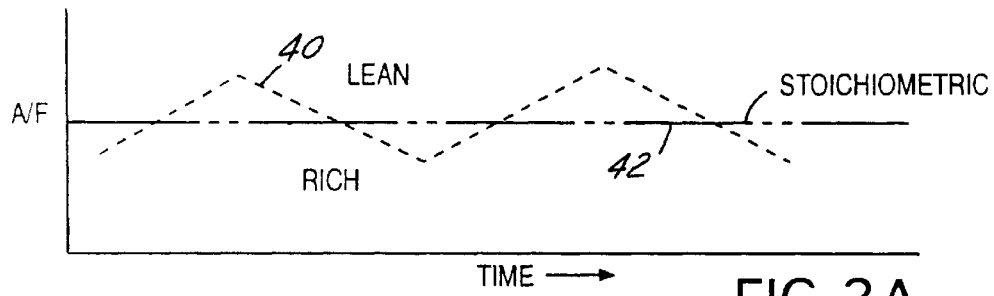
FIG. 2A is graph illustrating the air/fuel (A/F) ratio relative to time as compared to stoichiometry.

The graph in FIG. 2A shows an example of variations between air/fuel (A/F) mixtures in an exhaust stream as a function of time, under feedback control from the sensor to the engine controller. When the engine controller makes an adjustment, the air/fuel mixture 40 approaches stoichiometry 42. However, the engine controller typically overcompensates by a little and perfect stoichiometry can never be constant. Thus, engine operation generally will move back and forth between slightly rich and slightly lean operation.

Figure 2B:
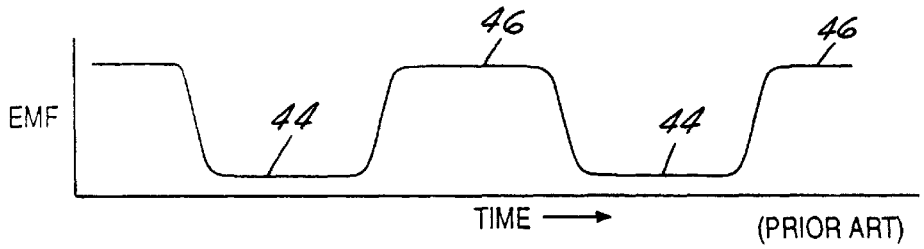
FIG. 2B is a graph illustrating a prior art emf (voltage) output versus time for a conventional Heated exhaust gas oxygen sensor, for the air/fuel ratios of FIG. 2A.

The second graph, FIG. 2B, shows the emf versus time for a conventional HEGO sensor mounted in an exhaust stream having the air/fuel ratios of FIG. 2A. The plateaus and flat values in between relate to the air/fuel mixture as compared to stoichiometry. The conventional EGO sensor has a relatively constant and high emf value 46 (e.g., between 700 and 900 mV) when the air/fuel ratio is rich and a relatively constant and low emf value 44 (e.g., 0 to 100 mV) when the air/fuel ratio is lean. When the air/fuel ratio is changed through stoichiometry, the emf of the sensor changes abruptly between a low and a high value. Because of the on-off characteristic of the output of the conventional sensor, the air/fuel feedback control is of the limit-cycle type rather than a proportional control. The air/fuel ratio is continuously ramped from a rich to lean or from lean to rich by the engine controller until the sensor senses passage through the stoichiometric air/fuel mixture. When this happens, the engine controller changes the direction of the ramping. As a result, the air/fuel ratio hovers around stoichiometry at a so-called limit-cycle frequency.

Figure 2C:
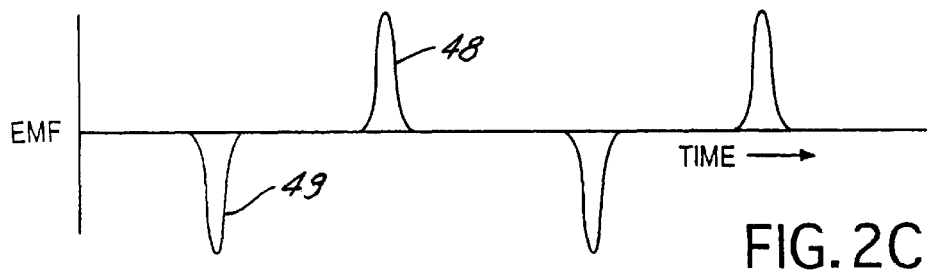
FIG. 2C is graph illustrating an emf (voltage) output versus time for the oxygen sensor of the present invention, for the air/fuel ratios of FIG. 2A.

FIG. 2C illustrates the induced emf versus time for the sensor 10 of the present invention, as illustrated in FIG. 1, as the air/fuel ratio, illustrated in FIG. 2A, switches between rich and lean. Note, the emf produced between the leads 24, 26 is not driven by a power source, rather it is induced by the sensor itself due to the difference created by the change in the air/fuel mixture depending on whether the last sharp voltage was negative or positive.

Figure 3:
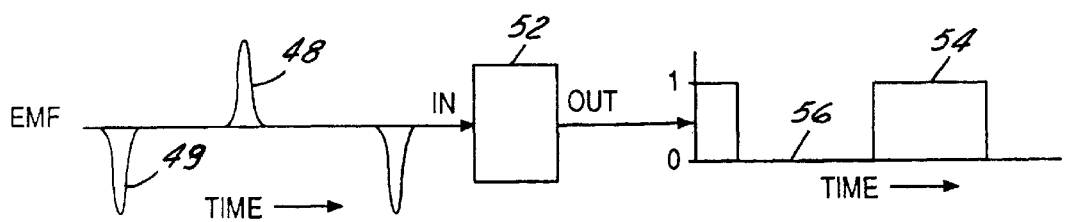
FIG. 3 is a schematic representation of an alternate embodiment illustrating conversion from the emf signal of FIG. 2C to an output signal in a square wave form after processing.

FIG. 3 illustrates an alternate embodiment of the present invention wherein a latch 52 is either connected to the nodes 28 and 30, as seen in FIG. 1, prior to a signal being fed into the signal processor 32 or where this latch is built into the signal processor. This embodiment can be used if one wishes to allow for the conversion of the signal produced by the sensor of the present invention (FIG. 2C) to imitate the signal of a conventional HEGO sensor, as seen in FIG. 2B, in order to take advantage of processors already used for processing the conventional signal. To accomplish this, the digital latch 52 is used. For the digital latch 52, the output is set to one 54 when a positive voltage with a magnitude above a certain threshold is applied to the input, (set mode), the output is reset to zero 56 when the minus voltage with a magnitude below a certain threshold is applied to the input, (reset mode), and the latch retains the last binary state stored into it when a generally zero value is applied, (hold mode). The wave form is then used by the signal processor to adjust the air/fuel ratio.

Figure 4:
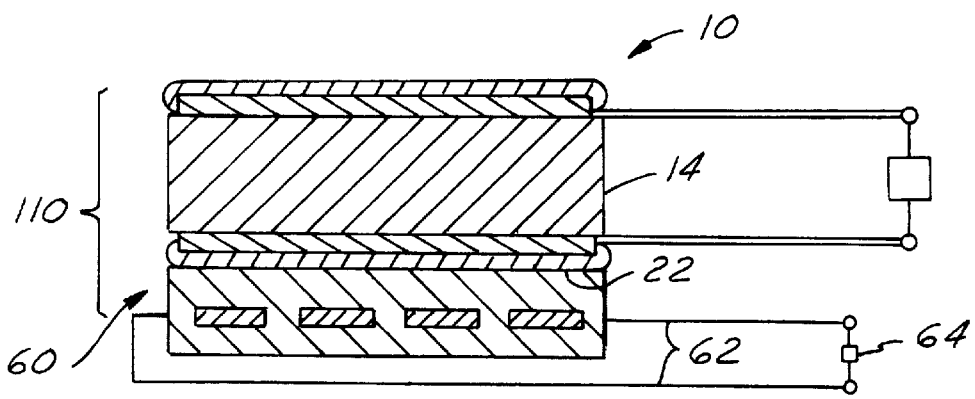
FIG. 4 is a view similar to FIG. 1 illustrating a further alternate embodiment of the present invention.

FIG. 4 illustrates another alternate embodiment of the present invention. This embodiment illustrates an oxygen sensor 10 similar to that in FIG. 1, but with an added heating element 60 to create a heated exhaust gas oxygen sensor (HEGO) assembly 110. For thins embodiment, modified elements from the first embodiment will have similar element numbers but with a 100 series number. For the added heater element 60, electrical connections 62 are made to a current supply 64. Since the overall sensor size can be very small and hence possesses a small thermal mass, only a small heating power is needed to provide a very rapid light-off time. For this embodiment, the heater element 60 can also be spaced apart slightly from the second porous layer 22 if so desired, although some separate support structure for the heating element would then be needed and the light-off time will be increased somewhat.

Figure 5:
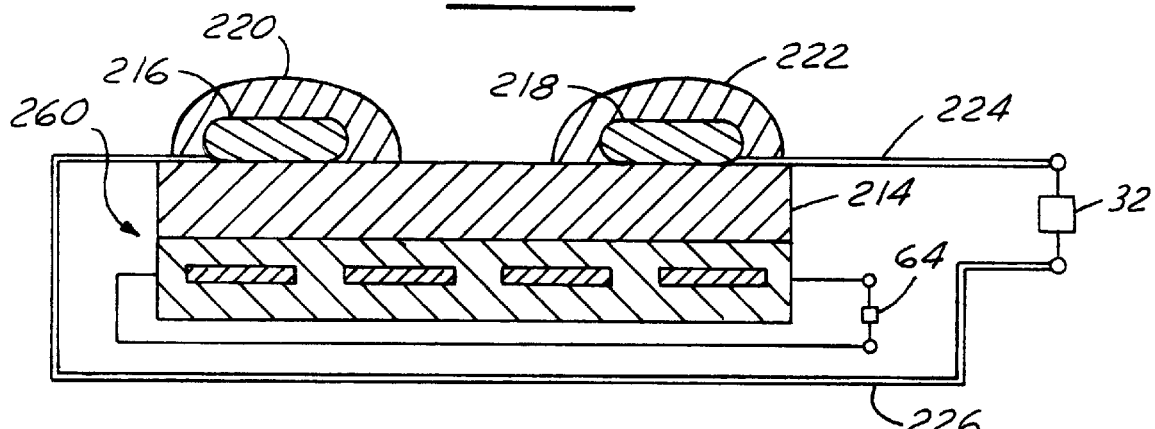
FIG. 5 is a view similar to FIG. 1 illustrating yet another alternate embodiment of the present invention.

FIG. 5 illustrates an additional embodiment of the present invention. For this embodiment, modified elements from the previous embodiments will have similar element numbers but with a 200 series number. The electrodes 216 and 218 and porous layers 220 and 222 are mounted on the same side of the plate 214, with leads 224 and 226 connecting to the signal processor 32. A heating element 260 is mounted on the side of the plate 214 opposite the electrodes 216,218. In this way, the heating element 260 is separated from both of the porous layers 220,222.

while certain embodiments of the present invention have been described in detail, those familiar with the art to which this invention relates will recognize various alternative designs and embodiments for practicing the invention as defined by the following claims.

We claim:

1. A method for detecting a change from lean to rich and rich to lean air/fuel ratio in the exhaust gas stream of an internal combustion engine comprising the steps of:

positioning an oxygen sensor in the exhaust gas stream, the oxygen sensor being formed having an oxygen-ion conducting solid electrolyte body with a first electrode assembly and a second electrode assembly mounted thereon, wherein the second electrode assembly is arranged to have a predetermined time difference in a gas transmission characteristic from the first electrode assembly;

periodically changing the air/fuel ratio of the exhaust gas stream from lean to rich and rich to lean;

inducing emf output spikes by the electrode assemblies when the exhaust gas stream transitions between rich and lean air/fuel ratios;

sensing the induced emf spikes output by the electrode assemblies;

creating an output signal with a positive value when a positive emf spike is sensed;

maintaining the output signal at the positive value until a negative emf spike is sensed;

changing the output signal to a value of about zero when the negative emf spike is sensed; and maintaining the output signal at the value of about zero until a positive emf spike is again sensed.

2. The method of claim 1 further including the step of heating the oxygen sensor until it has reached a desired temperature.

3. The method of claim 1 further including the steps of: increasing the air/fuel ratio when the emf spike induced is a positive value and decreasing the air/fuel ratio when the emf spike induced is a negative value.

* * * * *